United States Patent [19]

Husbands

[11] Patent Number: 4,609,758

[45] Date of Patent: Sep. 2, 1986

[54] PHENOXYETHYLAMINE DERIVATIVES

[75] Inventor: George E. M. Husbands, Berwyn, Pa.

[73] Assignee: American Home Products Corporation, New York, N.Y.

[21] Appl. No.: 732,478

[22] Filed: May 9, 1985

[51] Int. Cl.[4] ............... C07C 93/06; C07C 103/26
[52] U.S. Cl. ..................... 564/348; 564/347; 564/171; 560/142; 560/252; 514/651
[58] Field of Search .............. 564/348, 171, 347; 560/142, 252; 514/651

[56] References Cited

U.S. PATENT DOCUMENTS 4,018,895  4/1977  Molloy et al. ............... 514/651

FOREIGN PATENT DOCUMENTS 3017812  11/1981  Fed. Rep. of Germany ...... 514/651

OTHER PUBLICATIONS

Sindelar et al., Coll. Czech. Chem. Commun., 46, 597 (1981).
Wong et al., J. Pharmacol. Exp. Ther., 222, 61–65 (1982).

*Primary Examiner*—Charles F. Warren
*Assistant Examiner*—John A. Sopp
*Attorney, Agent, or Firm*—Richard K. Jackson

[57] ABSTRACT

This invention provides a group of hydroxycycloalkanephenoxyethylamine antidepressant derivatives of the following structural formula:

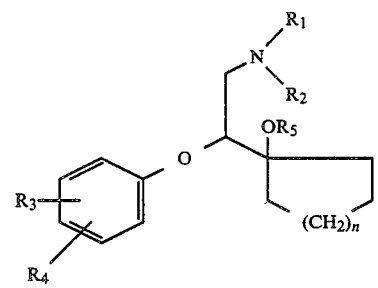

in which
 $R_1$ is hydrogen or alkyl of 1 to 6 carbon atoms;
 $R_2$ is alkyl of 1 to 6 carbon atoms;
 $R_3$ and $R_4$ are independently hydrogen, hydroxyl, alkyl of 1 to 6 carbon atoms, alkoxy of 1 to 6 carbon atoms, alkanoyloxy of 2 to 7 carbon atoms, halo or trifluoromethyl;
 $R_5$ is hydrogen, alkyl of 1 to 6 carbon atoms or alkanoyl of 2 to 7 carbon atoms;
 and n is one of the integers 0, 1, 2 or 3;
or a pharmaceutically acceptable salt thereof.

16 Claims, No Drawings

PHENOXYETHYLAMINE DERIVATIVES

DESCRIPTION OF THE INVENTION

In accordance with this invention there is provided a group of substituted phenoxyethylamine derivatives which are central nervous system antidepressants. The compounds of this invention present the following structural formula:

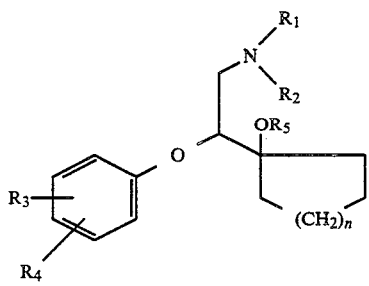

in which
- $R_1$ is hydrogen or alkyl of 1 to 6 carbon atoms;
- $R_2$ is alkyl of 1 to 6 carbon atoms;
- $R_3$ and $R_4$ are independently hydrogen, hydroxyl, alkyl of 1 to 6 carbon atoms, alkoxy of 1 to 6 carbon atoms, alkanoyloxy of 2 to 7 carbon atoms, halo or trifluoromethyl;
- $R_5$ is hydrogen, alkyl of 1 to 6 carbon atoms or alkanoyl of 2 to 7 carbon atoms;
- and n is one of the integers 0, 1, 2 or 3;

or a pharmaceutically acceptable salt thereof.

The compounds in which $R_5$ is alkanoyl of 2 to 7 carbon atoms are less potent than those where $R_5$ is hydrogen. However, in long term therapy the acyloxy derivatives will act as pro drugs as the acyl group may be removed in vivo either via acid hydrolysis in the stomach or enzymatically.

The pharmaceutically acceptable acid addition salts of the basic compounds of this invention are formed conventionally by reaction of the free base with an equivalent amount of any acid which forms a non-toxic salt. Illustrative acids are either inorganic or organic, including hydrochloric, hydrobromic, fumaric, maleic, succinic, sulfuric, phosphoric, tartaric, acetic, citric, oxalic and similar acids. For parenteral administration, the use of water soluble salts is preferred, although either the free base of the pharmaceutically accpetable salts are applicable for oral or parenteral administration of the antidepressant agents of this invention. The halo substituent representing $R_3$ or $R_4$ is intended to inclue the chloro, bromo, iodo or fluoro substituents.

The preferred compounds are those of the formula:

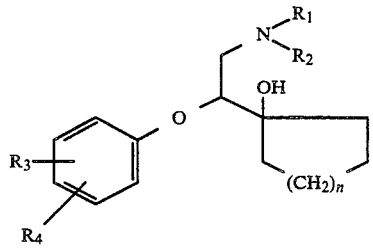

in which
- $R_1$ is alkyl of 1 to 3 carbon atoms;
- $R_2$ is alkyl of 1 to 3 carbon atoms;
- $R_3$ is hydrogen, alkoxy of 1 to 3 carbon atoms, chloro, bromo or trifluoromethyl;
- $R_4$ is alkyl of 1 to 3 carbon atoms, alkoxy of 1 to 3 carbon atoms, chloro, bromo or trifluoromethyl;
- and n is one of the integers 1, 2 or 3;

or a pharmaceutically acceptable salt thereof.

The most preferred compounds are those in which $R_3$ and $R_4$ are in meta or para positions.

The compounds of this invention are prepared by reaction of a cycloalkanone with an appropriately substituted phenoxyacetamide anion following the procedure of Sauvetre et al., Tetrahedron, 34, 2135 (1978), followed by reduction of the amide with aluminum hydride or a borane reducing agent to the corresponding amine. This method permits one to readily vary the valued $R_1$ and $R_2$ in the initial reactant.

The intermediate amide represents an additional aspect of this invention and is depicted by the following structural formula:

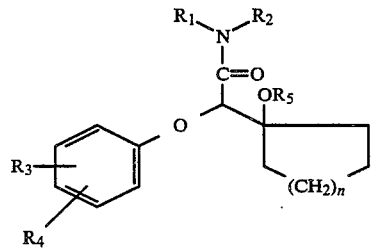

in which
- $R_1$ is hydrogen or alkyl of 1 to 6 carbon atoms;
- $R_2$ is alkyl of 1 to 6 carbon atoms;
- $R_3$ and $R_4$ are, independently, hydrogen, hydroxyl, alkyl of 1 to 6 carbon atoms, alkoxy of 1 to 6 carbon atoms, alkanoyloxy of 2 to 7 carbon atoms, halo or trifluoromethyl;
- $R_5$ is hydrogen or alkyl of 1 to 6 carbon atoms;
- and n is one of the integers 0, 1, 2 or 3.

When $R_5$ is alkyl it is introduced prior to reduction of the carbonyl group by conventional O-alkylation.

During the course of the synthesis of the compounds of this invention any hydroxy group represented by —$OR_5$, $R_3$ or $R_4$ may be in the free form or in the form of hydroxy protected by a removable protecting group, except of course, that the hyroxy group is not protected in any case where it is intended to participate in a reaction. The protected form is recommended where the hydroxy group may otherwise undergo an undesired reaction. Examples of protecting groups for hydroxy are given in Protective Groups in Organic Chemistry edited by J. F. W. McOmie, Chapters 3 and 4 (pages 95-182), published by Plenum Press (1973), and Protective Groups in Organic Chemistry by T. W. Greene, Chapters 2 and 3 (pages 10 to 113) published by John Wiley and Sons (1981). The protecting group may be removed at a suitable later stage in the synthesis.

The end products contain one asymmetric center. Individual stereoisomeric forms may be obtained or separated by standard procedures. For instance, separation of the mixture may be carried out by neutralization with a suitable optically active compound to form salts which can be separated.

The antidepressant activity of the compounds of this invention was established by demonstrating that they inhibit synaptosomal uptake of norepinephrine ($^3$H-NE) and serotonin ($^{14}$C-5-HT) following the test procedure of Wood et al., J. Neurochem., 37, 795-797 (1981).

The results of these procedures affirmed the antidepressant activity of the compounds of this invention agreement with the most widely accepted theory of antidepressant activity and in correlation of activity with known tricyclic antidepressants. In at least two instances, namely, with the 2,4-dichloro product of Example 2, and 4-chloro product in Example 1, the undesirable attribute of classical antidepressants observed as an anticholinergic property which is reflected by the inhibition of binding of the muscarinic receptor ligand, 3-H-quinuclidinyl benzilate (QNB) is missing.

Inhibition of synaptosomal NE and 5-HT uptake: Results of the inhibition of NE and 5-HT synaptosomal uptake, expressed as the inhibitory concentration at which the rate of uptake was reduced to 50 percent ($IC_{50}$), are presented in the table below, where they are compared with the values for imipramine, DMI, amitriptyline and fluoxetine:

| Compound | NE | 5-HT |
|---|---|---|
| Imipramine | 0.26 | 0.12 |
| DMI | 0.15 | 3.0 |
| Amitriptyline | 0.50 | 0.60 |
| Fluoxetine | 4.5 | 0.14 |
| Example 1 | 0.22 | 0.17 |
| Example 2 | 3.14 | 0.53 |
| Example 3 | 2.25 | 0.44 |
| Example 4 | 0.92 | 0.18 |
| Example 5 | 0.81 | 0.17 |
| Example 6 | 3.14 | 0.64 |
| Example 7 | 2.35 | 1.2 |
| Example 8 | 2.5 | 0.34 |
| Example 9 | 3.78 | 0.49 |
| Example 10 | 1.16 | 0.7 |
| Example 11 | 1.16 | 0.9 |
| Example 12 | 1.58 | 0.97 |

Inhibition of $^3$H-QNB binding: In the QNB receptor binding assay, the Compounds from Examples 1 and 2 exhibited an $IC_{50}$ greater than $10^{-5}$ molar and were therefore essentially inactive. Imipramine and DMI exhibit $K_i$'s of 37 nM and 50 nM, respectively. These results suggest that, unlike the tricyclic antidepressants, Compounds of Example 1 and 2 would have no muscarinic anticholinergic actions.

Hence, the end compounds of this invention are useful in the treatment of depression, for which purpose they may be administered orally or parenterally in an amount sufficient to alleviate the symptoms of depression. The actual amount of antidepressant agent to be used will vary with the severity and nature of the depressed state, the animal being treated and the level of relief sought. In the human, an oral dose of from about 2 to about 50 milligrams, administered as needed represents appropriate posology. Intramuscular administration of from about 1 to about 25 milligrams provides a dosage comparable to that specified for oral administration. As with other antidepressants, therapy should be initiated with lower dosages and increased until the desired symptomatic relief is obtained.

Pharmaceutical compositions containing the antidepressant compounds of this invention represent an additional aspect of this invetnion. The active ingredient can be compounded into any of the usual oral dosage forms including tablets, capsules and liquid preparations such as elixirs and suspensions containing various coloring, flavoring, stabilizing and flavor masking substances. For compounding oral dosage forms, the active ingredient can be mixed with various conventional tabletting materials such as starch, calcium carbonate, lactose, sucrose and dicalcium phosphate to aid the tabletting or capsulating process. Magnesium stearate, as an additive, provides a useful lubricant function when desired.

The active ingredients can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal silane as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances other compositions can be made by dispersinag the finely-divided active ingredient in aqueous starch or sodium carboxymethylcellulose solution, or in a suitable oil, for instance arachis oil. Liquid pharmaceutical compositions which are sterile solutions or suspensions can be utilised by intramuscular, intraperitoneal or subcutaneous injection.

Preferably the pharmaceutical composition is in unit dosage form, e.g. as tablets or capsules. In such form, the composition is sub-divided in unit doses containing appropriate quantities of the active ingredient; the unit dosage forms can be packaged compositions, for example, packeted powders or vials or ampoules. The unit dosage form can be a capsule, cachet or tablet itself, or it can be the appropriate number of any of these in package form. The quantity of the active ingredient in a unit dose of composition may be vaired or adjusted from 2 mg. or less to 50 mg. or more, according to the particular need and the activity of the active ingredient. The following examples illustrate the preparative technique employed in production of the compounds of the invention.

EXAMPLE 1

1-[1-(4-Chlorophenoxy)-2-(dimethylamino)ethyl]cyclohexanol

Para chlorophenoxy acetic acid (25 g, 0.134 mole) was dissolved in methylene chloride (500 ml) and treated with oxalyl chloride (13.4 ml, 0.15 mole) and dimethylformamide (0.5 ml) at room temperature. The mixture was stirred for three hours until gas evolution ceased. The solvent was evaporated and the residue dried under vacuum to remove excess oxalyl chloride. The residue was dissolved in methylene chloride (300 ml) and treated with gaseous dimethylamine. The mixture was stirred overnight and the solvent evaporated. The residue was redissolved in methylene chloride (200 ml) and the solution washed with saturated sodium bicarbonate solution, water, N-hydrochloric acid, water, brine, dried over magnesium sulfate and evaporated. The product, 2-(4-chlorophenoxy)-N,N-dimethyl acetamide, crystallized and was washed with hexane and air dried. Yield: 17.2 g, m.p. 69°–71° C.

Analysis for: $C_{10}H_{12}NO_2Cl$: Calculated: C, 56.21; H, 5.66; N, 6.56; Found: C, 55.65; H, 5.63; N, 6.57.

Lithium di-isopropylamide was prepared by dissolving di-isopropylamine (11 ml) in tetrahydrofuran (150 ml) followed by the addition of n-butyl lithium (50 ml of 1.7 molar). After 10 minutes stirring, the straw colored liquid was cooled to $-78°$ C. and a solution of 2-(4-chlorophenoxy)-N,N-dimethyl acetamide (16 g, 0.074 mole) in tetrahydrofuran (25 ml) was slowly added. The mixture was stirred for 20 minutes at $-78°$ C. and cyclohexanone (7 ml) added. After 45 minutes at $-78°$ C., the reaction mixture was poured into saturated ammonium chloride solution and a red color ensued. The phases were separated and the organic layer washed with brine, dried over anhydrous potassium carbonate and evaporated giving 1-[(4-chlorophenoxy)((dimethylamino)carbonyl)methyl]cyclohexanol as a red solid. Repeated washing with a cold hexane-isopropanol mixture yielded 2.7 g of a white crystalline solid. Yield: 2.7 g, m.p. 109°–111° C.

Analysis for: $C_{16}H_{22}NO_3Cl$: Calculated: C, 61.63; H, 7.11; N, 4.49; Found: C, 61.01; H, 6.91; N, 4.63.

Lithium aluminum hydride (0.6 g) was suspended in dry tetrahydrofuran (20 ml) cooled to 0° C. and concentrated sulfuric acid (0.42 ml) was cautiously added in an in situ preparation of aluminum hydride. The mixture was stirred for one hour at 0° C. and 1-[(4-chlorophenoxy)((dimethylamino)carbonyl)methyl]cyclohexanol (2.7 g, 0.009 mole) was dissolved in tetrahydrofuran (10 ml) and added. The reaction mixture was maintained below 10° C. and stirred for one hour. The reaction mixture was cooled to 0° C. and a tetrahydrofuran-water mixture (5 ml, 1:1 v/v) added slowly. Ten percent sodium hydroxide (5 ml) was next added and the mixture filtered. The filtrate was dried over anhydrous potassium carbonate and evaporated. The residue was dissolved in ethyl acetate and the solution treated with 4 N-isopropanolic HCl whereupon the title compound as the hydrochloride salt separated. The salt was filtered, washed with acetone, ethyl acetate, diethyl ether and petroleum ether and air dried. Yield: 530 mg, m.p. 218°–220 C.

Analysis for: $C_{16}H_{24}NO_2Cl.HCl.\frac{1}{2}H_2O$: Calculated: C, 55.98; H, 7.63; N, 4.08; Found: C, 55.97; H, 7.26; N, 3.9.

NMR Analysis (DMSO): 7.28 (4H quartet, aromatic) 4.72 (1H triplet, O—CH—CH$_2$—) 3.5 (2H doublet, O—CH—CH$_2$) 2.86 (6H singlet, —N(CH$_3$)$_2$) 1.4 (10H multiplet, aliphatic cyclohexyl) ppm.

EXAMPLE 2

1-[1-(2,4-Dichlorophenoxy)-2-(dimethylamino)ethyl]cyclohexanol

By replacing p-chlorophenoxy acetic acid in Example 1 with a molar equivalent amount of 2,4-dichlorophenoxy acetic acid and following the procedure described therein, 1-[1-(2,4-dichlorophenoxy)-2-(dimethylamino)ethyl]cyclohexanol was obtained and converted to the hydrochloride salt using 4 N-isopropanolic HCl, m.p. 230°–232° C.

Analysis for: $C_{16}H_{23}NO_2Cl_2.HCl$: Calculated: C, 52.18; H, 6.55; N, 3.79; Found: C, 51.97; H, 6.39; N, 3.78.

EXAMPLE 3

8-[1-(2,4-Dichlorophenoxy)-2-(dimethylamino)ethyl]cyclopentanol

By replacing cyclohexanone in Example 2 with a molar equivalent amount of cyclopentanone, the title compound was obtained and converted to the hydrochloride salt using 4 N-isopropanolic HCl, m.p. 174°–175° C.

Analysis for: $C_{15}H_{21}NO_2Cl_2.HCl$: Calculated: C, 50.79; H, 6.25; N, 3.95; Found: C, 50.81; H, 6.24; N, 3.97.

EXAMPLE 4

1-[2-(Dimethylamino)-1-(4-methoxyphenoxy)ethyl]cyclohexanol

By replacing p-chlorophenoxy acetic acid with a molar equivalent amount of p-methoxyphenoxy acetic acid in Example 1 and following the procedure described therein, 1-[[(dimethylamino)carbonyl][4-methoxyphenoxy]methyl]cyclohexanol was obtained as a crystalline solid, m.p. 98°–99° C.

Analysis for: $C_{17}H_{25}NO_4$: Calculated: C, 66.42; H, 8.20; N, 4.86; Found: C, 66.14; H, 8.12; N, 4.54.

To a solution of Borane/tetrahydrofuran complex (50 ml, 50 mmole) was added a solution of 1-[[(dimethylamino)carbonyl][4-methoxyphenoxy]methyl]cyclohexanol (5 g, 16.3 mmole) in dry tetrahydrofuran (25 ml). The mixture was refluxed for one hour, and cooled in an ice bath. 6N HCl (18 ml) was added and the solution refluxed for one hour. The solution was then cooled in an ice bath, basified with solid potassium hydroxide and the two layers separated. The organic layer was washed with brine, dried over magnesium sulfate and evaporated. The solid residue was dissolved in diethyl ether and 4N-isopropanolic HCl was added. The title compound, as the hydrochloride salt, was washed well with diethyl ether, acetone, ethyl acetate and petroleum ether, and dried in a desiccator under vacuum. Yield: 3.52 g; m.p. 196°–198° C.

Analysis for: $C_{17}H_{27}NO_3 \cdot HCl$: Calculated: C, 61.90; H, 8.56; N, 4.25; Found: C, 61.52; H, 8.51; N, 4.36.

NMR Analysis (DMSO): 7.0 (4H, aromatic) 4.38 (1H, OC$\underline{H}$H—CH$_2$) 3.76 (3H singlet, —OMe) 3.54 (2H, O—CH—C$\underline{H}_2$) 2.86 (6H singlet, N(CH$_3$)$_2$) 1.5 (10H multiplet, aliphatic cyclohexyl) ppm.

EXAMPLE 5

1-[2-(Dimethylamino)-1-(4-methoxyphenoxy)ethyl]cycloheptanol

By replacing cyclohexanone with a molar equivalent amount of cycloheptanone in Example 4, the title compound was obtained and converted to the hydrochloride, m.p. 185°–186° C.

Analysis for: $C_{18}H_{29}NO_3 \cdot HCl$: Calculated: C, 62.86; H, 8.79; N, 4.07; Found: C, 62.87; H, 8.84; N, 3.92.

EXAMPLE 6

1-[2-(dimethylamino)-1-(4-methoxyphenoxy)ethyl]cyclopentanol

By replacing cyclohexanone with a molar equivalent amount of cyclopentanone in Example 4 the title compound was obtained and converted to the hydrochloride, m.p. 167°–168° C.

Analysis for: $C_{16}H_{25}NO_3 \cdot HCl$: Calculated: C, 60.85; H, 8.30; N, 4.43; Found: C, 60.37; H, 8.20; N, 4.57.

EXAMPLE 7

1-[2-(dimethylamino)-1-(3-trifluoromethylphenoxy)ethyl]cyclohexanol m-Hydroxybenzotrifluoride (8.5 ml, 70 mmole) was dissolved in absolute ethanol (50 ml) and solid potassium hydroxide (3.92 g) added. The mixture was stirred until solution was complete and the solvent was evaporated. The residue, a red oil, was dissolved in 2-butanone (80 ml). Potassium iodide (2 g) and 2-chloro-N,N-dimethylacetamide (7.9 g, 65 mmole) were added and the mixture refluxed overnight. The reaction mixture was then cooled in ice and filtered. The filtrate was evaporated and the residue obtained partitioned between diethyl ether and 5% sodium hydroxide. The organic layer was washed with water, brine, dried over magnesium sulfate and evaporated. N,N-dimethyl-2-[3-(trifluoromethyl)phenoxy]acetamide was obtained as a yellow solid. Yield: 13.8 g, m.p. 88.5°–89.5° C.

Analysis for: $C_{11}H_{12}NO_2F_3$: Calculated: C, 53.44; H, 4.89; N, 5.67; Found: C, 53.01; H, 4.85; N, 5.55.

N,N-dimethyl-2-[3-trifluoromethyl)phenoxy]acetamide, prepared from 2-[3-trifluoromethylphenoxyl]acetic acid in accordance with Example 1 was converted to the amide which was reduced with Borane/tetrahydrofuran as in Example 3. The title compound was obtained and its hydrochloride salt prepared, m.p. 210°–211° C.

Analysis for: $C_{17}H_{24}NO_2F_3 \cdot HCl$: Calculated: C, 55.51; H, 6.85; N, 3.81; Found: C, 55.75, H, 6.81; N, 4.04.

EXAMPLE 8

1-[2-Dimethylamino-1-(4-trifluoromethylphenoxy)ethyl]cyclohexanol

By replacing m-hydroxybenzotrifluoride with a molar equivalent amount of p-hydroxybenzotrifluoride in Example 7, the title compound was obtained and its hydrochloride salt prepared, m.p. 251°–252° C.

Analysis for: $C_{17}H_{24}NO_2F_3 \cdot HCl$: Calculated: C, 55.56; H, 6.80; N, 3.87; Found: C, 55.36; H, 6.78; N, 3.72.

EXAMPLE 9

1-[2-Dimethylamino-1-(4-trifluoromethylphenoxy)ethyl]cycloheptanol

By replacing cyclohexanone with a molar equivalent amount of cycloheptanone in Example 7, the title compound was obtained and characterized as its hydrochloride salt, m.p. 210°–212° C.

Analysis for: $C_{18}H_{26}NO_2F_3 \cdot HCl \cdot \frac{1}{2}C_3H_8O$: Calculated: C, 56.86; H, 7.59; N, 3.40; Found: C, 57.34; H, 7.40; N, 3.47.

EXAMPLE 10

1-[2-(Dimethylamino)-1-(3-methoxyphenoxy)ethyl]cyclohexanol

By replacing p-methoxyphenoxy acetic acid with a molar equivalent of m-methoxyphenoxy acetic acid in Example 4, the title compound was obtained and the hydrochloride prepared.

Analysis for: $C_{17}H_{27}NO_3 \cdot HCl$: Calculated: C, 61.90; H, 8.25; N, 4.25; Found: C, 61.45; H, 8.46; N, 4.51.

EXAMPLE 11

1-[2-(Dimethylamino)-1-(3-methoxyphenoxy)ethyl]cycloheptanol

By replacing cyclohexanone with a molar equivalent amount of cycloheptanone in Example 10, the title compound was obtained and its hydrochloride salt prepared.

Analysis for: $C_{18}H_{29}NO_3 \cdot HCl$: Calculated: C, 62.87; H, 8.5; N, 4.07; Found: C, 62.16; H, 8.6; N, 4.13.

EXAMPLE 12

1-[2-(Dimethylamino)-1-(3-methoxyphenoxy)ethyl]cyclopentanol

By replacing cyclohexanone with a molar equivalent of cyclopentanone in Example 10, the title compound was obtained and its hydrochloride prepared, m.p. 168°–169° C.

Analysis for: $C_{16}H_{25}NO_3 \cdot HCl$: Calculated: C, 60.85; H, 8.30; N, 4.43; Found: C, 60.38; H, 8.28; N, 4.62.

What is claimed is:

1. A compound of the formula:

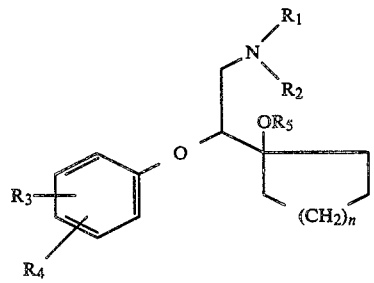

in which $R_1$ is hydrogen or alkyl of 1 to 6 carbon atoms;

$R_2$ is alkyl of 1 to 6 carbon atoms;

$R_3$ and $R_4$ are independently hydrogen, hydroxyl, alkyl of 1 to 6 carbon atoms, alkoxy of 1 to 6 carbon atoms, alkanoyloxy of 2 to 7 carbon atoms, halo or trifluoromethyl;

$R_5$ is hydrogen, alkyl of 1 to 6 carbon atoms or alkanoyl of 2 to 7 carbon atoms;

and n is one of the integers 0, 1, 2 or 3; or a pharmaceutically acceptable salt thereof.

2. A compound of claim 1 in which $R_1$ is alkyl of 1 to 3 carbon atoms; $R_2$ is alkyl of 1 to 3 carbon atoms; $R_3$ is hydrogen, alkoxy of 1 to 3 carbon atoms, chloro, bromo or trifluoromethyl; $R_4$ is alkyl of 1 to 3 carbon atoms, alkoxy of 1 to 3 carbon atoms, chloro, bromo or trifluoromethyl; $R_5$ is hydrogen; and n is one of the integers 1, 2 or 3; or a pharmaceutically acceptable salt thereof.

3. A compound of claim 2 in which $R_3$ and $R_4$ are in meta or para positions.

4. The compound of claim 1 which is 1-1[1-(4-chlorophenoxy)-2-(dimethylamino)ethyl]cyclohexanol or a pharmaceutically acceptable salt thereof.

5. The compound of claim 1 which is 1-[1-(2,4-dichlorophenoxy)-2-(dimethylamino)ethyl]cyclohexanol or a pharmaceutically acceptable salt thereof.

6. The compound of claim 1 which is 1-[1-(2,4-dichlorophenoxy)-2-(dimethylamino)ethyl]cyclopentanol or a pharmaceutically acceptable salt thereof.

7. The compound of claim 1 which is 1-[2-(dimethylamino)-1-(4-methoxyphenoxy)ethyl]cyclohexanol or a pharmaceutically acceptable salt thereof.

8. The compound of claim 1 which is 1-[2-(dimethylamino)-1-(4-methoxyphenoxy)ethyl]cycloheptanol or a pharmaceutically acceptable salt thereof.

9. The compound of claim 1 which is 1-[2-(dimethylamino)-1-(4-methoxyphenoxy)ethyl]cyclopentanol or a pharmaceutically acceptable salt thereof.

10. The compound of claim 1 which is 1-[2-(dimethylamino)-1-(3-trifluoromethylphenoxy)ethyl]cyclohexanol or a pharmaceutically acceptable salt thereof.

11. The compound of claim 1 which is 1-[2-dimethylamino-1-(4-trifluoromethylphenoxy)ethyl]cyclohexanol or a pharmaceutically acceptable salt thereof.

12. The compound of claim 1 which is 1-[2-dimethylamino-1-(4-trifluoromethylphenoxy)ethyl]cycloheptanol or a pharmaceutically acceptable salt thereof.

13. The compound of claim 1 which is 1-[2-(dimethylamino)-1-(3-methoxyphenoxy)ethyl]cyclohexanol or a pharmaceutically acceptable salt thereof.

14. The compound of claim 1 which is 1-[2-(dimethylamino)-1-(3-methoxyphenoxy)ethyl]cycloheptanol or a pharmaceutically acceptable salt thereof.

15. The compound of claim 1 which is 1-[2-(dimethylamino)-1-(3-methoxyphenoxy)ethyl]cyclopentanol or a pharmaceutically acceptable salt thereof.

16. A compound of the formula

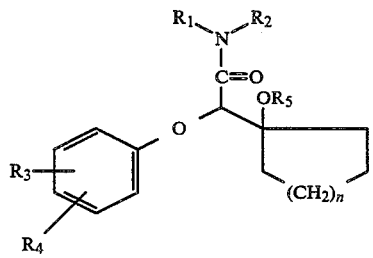

in which
$R_1$ is hydrogen or alkyl of 1 to 6 carbon atoms;
$R_2$ is alkyl of 1 to 6 carbon atoms;
$R_3$ and $R_4$ are, independently, hydrogen, hydroxyl, alkyl of 1 to 6 carbon atoms, alkoxy of 1 to 6 carbon atoms, alkanoyloxy of 2 to 7 carbon atoms, halo or trifluoromethyl;
$R_5$ is hydrogen or alkyl of 1 to 6 carbon atoms;
and n is one of the integers 0, 1, 2 or 3.

* * * * *